US00PP15812P2

(12) United States Plant Patent
Olesen et al.

(10) Patent No.: US PP15,812 P2
(45) Date of Patent: Jun. 28, 2005

(54) MINIATURE ROSE PLANT NAMED 'POULHI016'

(50) Latin Name: *Rosa hybrida*
Varietal Denomination: POULhi016

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 27 days.

(21) Appl. No.: 10/813,547

(22) Filed: Mar. 29, 2004

(51) Int. Cl.[7] ..... A01H 5/00
(52) U.S. Cl. ..... Plt./122
(58) Field of Search ..... Plt./129, 122

*Primary Examiner*—Anne Marie Grunberg
*Assistant Examiner*—June Hwu

(57) ABSTRACT

A new miniature rose plant which has abundant, red flowers and attractive foliage. The variety successfully propagates from softwood cuttings and is suitable for year round production in commercial glasshouses. This new and distinct variety has shown to be uniform and stable in the resulting generations from asexual propagation.

2 Drawing Sheets

Botanical classification: *Rosa hybrida.*
Variety denomination: 'POULhi016'.

SUMMARY OF THE INVENTION

The present invention constitutes a new and distinct variety of miniature rose plant which originated from a controlled crossing between the female seed parent an un-named seedling, and the male pollen parent, an un-named seedling. The two parents were crossed and the resulting seeds were planted in a controlled environment. The new variety is named 'POULhi016'.

The new rose may be distinguished from its seed parent by the following combination of characteristics:

1. The seed parent has flower petals which are lighter red in color than those of 'POULhi016'.
2. Flowers of the seed parent have fewer flower petals than those of 'POULhi016'.

The new variety may be distinguished from its pollen parent by the following combination of characteristics:

1. The pollen parent has a shorter growth habit than that of 'POULhi016'.
2. The pollen parent has flowers with fewer petals than flowers of 'POULhi016'.

The objective of the hybridization of this rose variety for commercial culture was to create a new and distinct variety with unique qualities, such as:

1. Uniform and abundant dark red flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry;
6. Disease resistance.

This combination of qualities is not present in previously available commercial cultivars of this type, known to the inventors, and distinguish 'POULhi016' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULhi016' was selected by the inventors as a single plant from the progeny of the hybridization in 1996.

Asexual reproduction of 'POULhi016' by cuttings and traditional budding was first done by L. Pernille and Mogens N. Olesen in their nursery in Fredensborg, Denmark in 1997. This initial and other subsequent propagations conducted in controlled environments have demonstrated that the characteristics of 'POULhi016' are true to type and are transmitted from one generation to the next.

BRIEF DESCRIPTION OF THE DRAWING

The accompanying color illustration shows as true as is reasonably possible to obtain in color photographs of this type, the typical characterictics of the buds, flowers, leaves, and stems of 'POULhi016'. Specifically illustrated in FIG. 1.

Figure 1:
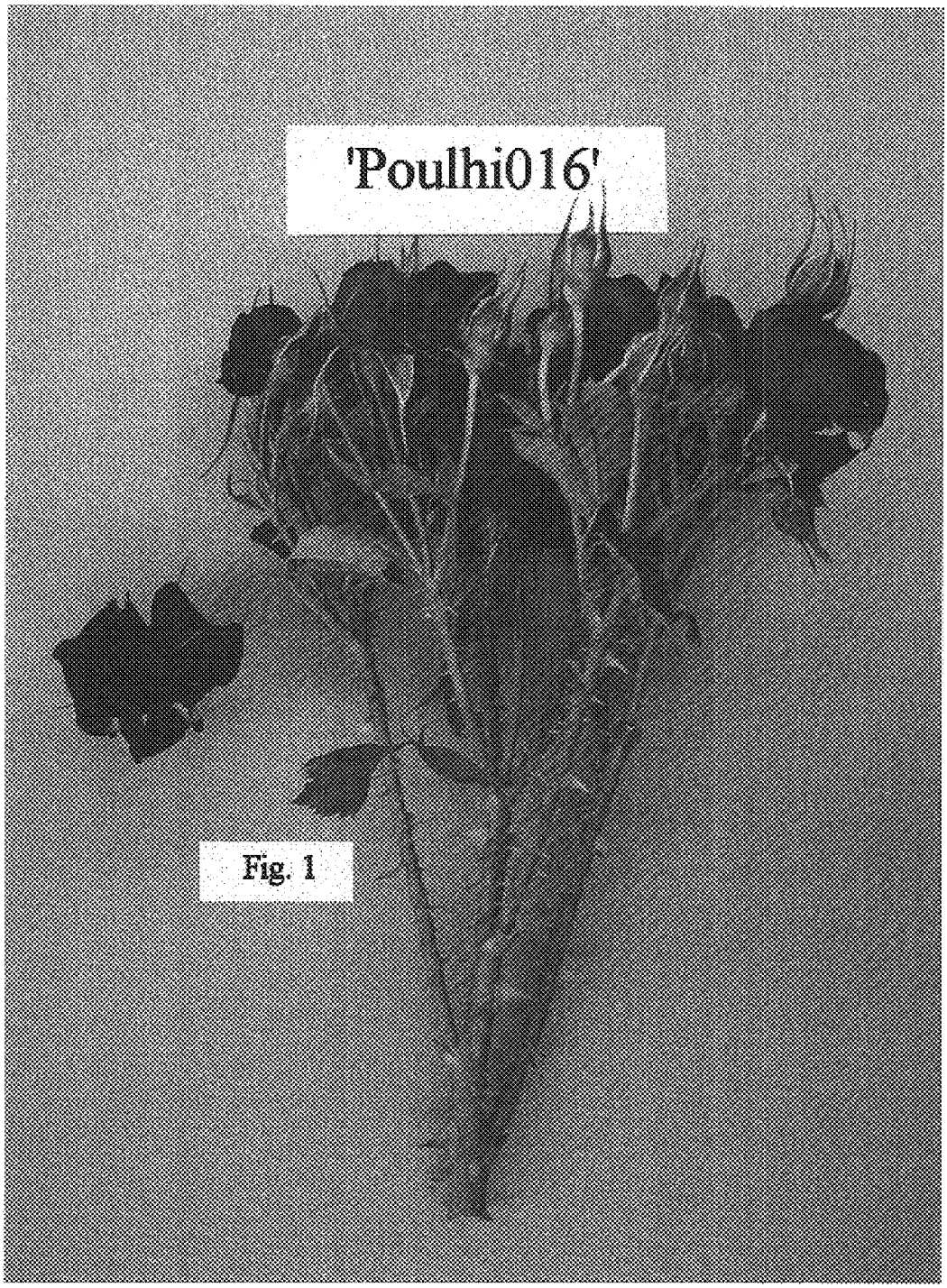
FIG. 1; Stem showing branching and the attachment of leaves, buds, and peduncles.

Specifically illustrated in FIG. 2:

FIG. 2.1; Flower petals, detached;
FIG. 2.2; Sepals, receptacle, and pedicel;
FIG. 2.3; Flower bud partially opened and opened;
FIG. 2.4; Bare stems exhibiting thorns;
FIG. 2.5; Trifoliate leaf.
FIG. 2.6; Mature leaves.

DETAILED DESCRIPTION OF THE VARIETY

The following is a description of 'POULhi016', as observed in its growth in Jackson County, Oreg. Observed plants are 3 years of age and were grown on *Rosa multiflora* rootstock. Color references are made using The Royal Horticultural Society (London, England) Colour Chart, 1995, except where common terms of color are used.

For a comparison, several physical characteristics of the rose variety 'POULanit', a rose variety from the same inventors described and illustrated in U.S. Plant Pat. No.

11,538 issued Oct. 3, 2000, are compared to 'POULhi016' in Chart 1.

CHART 1

| | 'Poulhi016' | 'Poulanit' |
|---|---|---|
| General tonality | 60A to Red Group 53A | Red Group 46A to 53A |
| Flower diameter | 30 to 35 mm | 45 to 55 mm |
| Petalage | 75 petals | 20 to 30 petals |

FLOWER AND FLOWER BUD

Blooming habit: Continuous.

Flower bud:

*Size.*—Upon opening, 22 mm in length from base of receptacle to end of bud. Bud diameter is 15 mm.

*Bud form.*—Globular.

*Bud color.*—As sepals unfold, Red-Purple Group 60A. Red-Purple Group 60A at ¼ opening.

*Sepals.*—Upper Surface: Color: Yellow-Green Group 145A. Surface: Surfaces of sepals strongly pubescent. Anthocyanin: Greyed-Red Group 178A. Lower Surface: Color: Yellow-Green Group 144A. Anthocyanin: Greyed-Orange Group 166A to Greyed-Purple Group 183A. Shape: Sepal apex is cirrhose. Base is flat at union with receptacle. Margins: Margins have weak foliaceous appendages on three of the five sepals. Stipitate glands are present in medium quantity on margins and lower surfaces of sepals. Size: 25 mm (l)×9 mm (w).

*Receptacle.*—Surface: Smooth and glaucous. Shape: Urn-shaped. Size: 8 mm (h)×8 mm (w). Color: Yellow-Green Group 144A. Anthocyanin: Greyed-Red Group 178A.

*Pedicel.*—Surface: Glaucous. Length: 30 to 35 mm. Color: Yellow-Green Group 144B. Anthocyanin: Greyed-Red Group 178A. Strength: Strong.

*Peduncle.*—Length: 50 to 70 mm. Diameter: 3 mm. Color: Yellow-Green Group 144A. Texture: Smooth, with many thorns. Strength: Strong.

*Borne.*—In small clusters. On average, there are 31 flower buds per flowering stem.

Flower bloom:

*Fragrance.*—Light floral scent.

*Duration.*—The blooms have a duration on the plant of approximately 10 to 14 days. Petals fall cleanly away from plant after flowers have fully matured.

*Size.*—Average flower diameter is 30 to 35 mm when open. Flower depth is 20 mm.

*Form.*—General shape is a deep cup. Shape of flower when viewed from the side: Upon opening, upper part: Flat. Upon opening, lower part: Convex. Open flower, upper part: Flattened convex. Open flower, lower part: Flattened convex.

*Petalage.*—On average 75 petals under normal conditions with 20 petaloids.

Color:

*Upon opening, petals.*—Outermost petals: Outer Side: Red-Purple Group 60A. Inner Side: Red Group 53A. Innermost petals: Outer Side: Red-Purple Group 60A. Inner Side: Red Group 53A.

*Upon opening, basal petal spots.*—Outermost petals: Outer Side: White Group 155A. Inner Side: White Group 155A. Innermost petals: Outer Side: White Group 155A. Inner Side: White Group 155A.

*After opening, petals.*—Outermost petals: Outer Side: Red-Purple Group 60A. Inner Side: Red Group 53A. Innermost petals: Outer Side: Red-Purple Group 60A. Inner Side: Red Group 53A.

*After opening, basal petal spots.*—Outermost petals: Outer Side: White Group 155A. Inner Side: White Group 155A. Innermost petals: Outer Side: White Group 155A. Inner Side: White Group 155A.

*Variations in petal color.*—Occasionally there are streaks the color of White Group 155A, appearing on the upper and lower surfaces of petals.

General tonality: On open flower Red-Purple Group 60A to Red Group 53A. No change in the general tonality at the end of the $10^{th}$ day.

Petals:

*Petal reflex.*—None.

*Petal margin.*—Entire with point in center of margin. Weak undulations of the margin observed.

*Form.*—Narrow elliptic.

*Shape.*—Base is acute. Apex is rounded.

*Size.*—25 mm (l)×24 mm (w).

*Thickness.*—Average.

*Arrangement.*—Not formal.

Petaloids:

*Quantity.*—15 to 25.

*Size.*—16 mm (l)×11 mm (w).

*Shape.*—Base is acute. Apex is rounded.

*Color.*—Upper Surface: Red Group 53A. Lower Surface: Red-Purple Group 60A.

Reproductive organs:

*Pistils.*—Length: 4 mm. Quantity: 35 (actual count).

*Pollen.*—None observed.

*Anthers.*—Size: 2 mm in length. Color: Greyed-Orange Group 163B. Quantity: 92 (actual count).

*Filaments.*—Color: Yellow-Green Group 145C to 145D with intonations of Red-Purple Group 60C. Length: 4 mm.

*Stigmas.*—Level with the height of the anthers. Color: Yellow-Green Group 145C.

*Styles.*—Length: 5 mm. Color: Yellow-Green Group 145C.

*Seed formation.*—Not observed.

PLANT

Plant growth: Vigorous, compact, upright to bushy. When grown in a field nursery on *Rosa multiflora* understock, the average height of the plant itself is 60 cm and the average width is 50 cm.

Stems:

*Color.*—Young wood: Yellow-Green Group 144B with light intonations of Greyed-Red Group 178A. Older wood: Yellow-Green Group 144A.

*Surface texture.*—Young wood: Smooth. Older wood: Smooth.

Thorns: Incidence: 130 thorns per 10 cm of stem. Size: Variable. 1 to 8 mm. Color: Yellow-Green Group 144B to Greyed-Red Group 178A. Shape: Concave.

Plant foliage: Normal number of leaflets on normal leaves in middle of the stem: 7 leaflets.

*Compound leaf size.*—160 mm (l)×100 mm (w).

*Quantity.*—Average.

*Color.*—Juvenile foliage: Upper Leaf Surface: Yellow-Green Group 146A to 147A. Lower Leaf Surface: Yellow-Green Group 147B. Mature foliage: Upper Leaf Surface: Yellow-Green Group 146A to 147A. Lower Leaf Surface: Yellow-Green Group 147B.

Anthocyanin intonation: Location: Underside and margins of juvenile foliage. Color: Greyed-Red Group 181A.

Plant leaves and leaflets:

*Stipules.*—Size: 20 mm in length. Shape: Linear with outward extending apecies. Quantity: Two per compound leaf. Margins: Finely serrated with few to many stipitate glands. Color: Yellow-Green Group 146B.

*Petiole.*—Length: 25 to 30 mm. Color: Yellow-Green Group 144B. Underneath: Thorns and stipitate glands present.

*Rachis.*—Size: 40 to 70 mm. Color: Yellow-Green Group 144B. Underneath: Thorns and stipitate glands present.

*Leaflet.*—Size: 41 mm (l)×26 mm (w). Edge: Serrated. General Shape: Broadly ovate. Apex Shape: Acute. Base Shape: Round. Texture: Smooth. Arrangement: Odd pinnate. Venation: Reticulate. Glossiness: Moderately glossy. Thickness: Thick.

Disease resistance: Average resistance to mildew, black spot, and Botrytis under normal growing conditions in Jackson County, Oreg.

Cold hardiness: 'POULhi016' has been found to be cold tolerant to USDA cold hardiness zone 6.

It is claimed:

1. A new and distinct variety of rose plant of the miniature class, substantially as herein illustrated and described as a distinct and novel rose variety due to its abundant, red flowers, vigorous growth, compact habit, suitability for production from softwood cuttings in pots, and durable flowers and foliage which make the variety suitable for distribution in the floral industry.

* * * * *

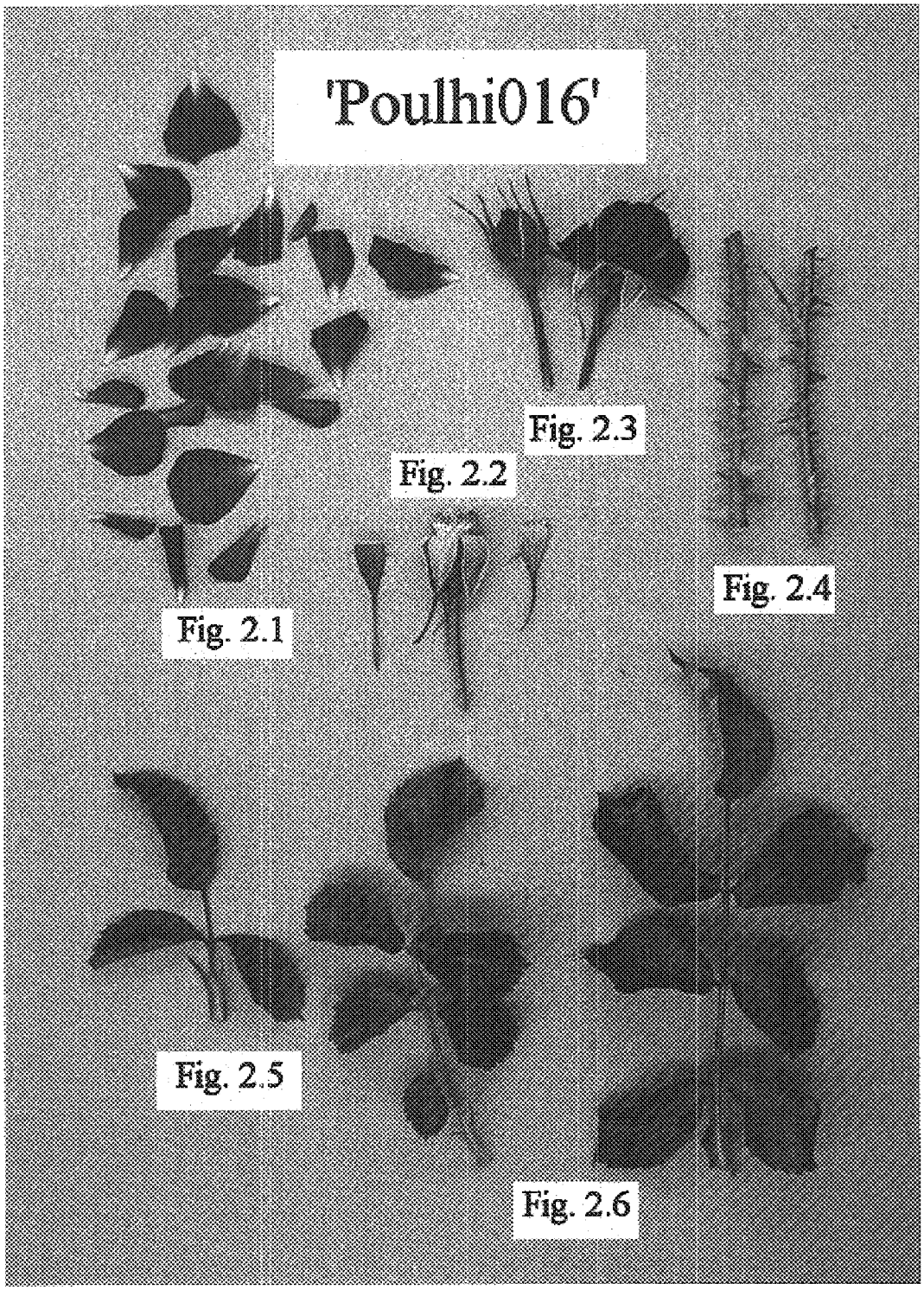
'Poulhi016'
Fig. 2.1
Fig. 2.2
Fig. 2.3
Fig. 2.4
Fig. 2.5
Fig. 2.6